United States Patent [19]

Bovenlander

[11] 4,257,258
[45] Mar. 24, 1981

[54] EXHAUST GAS ANALYZER FOR DIESEL ENGINES

[75] Inventor: Johannes P. Bovenlander, Krommenie, Netherlands

[73] Assignee: Sun Electric Europe B.V., Amsterdam, Netherlands

[21] Appl. No.: 68,650

[22] Filed: Aug. 22, 1979

[30] Foreign Application Priority Data

Aug. 23, 1978 [DE] Fed. Rep. of Germany ....... 2836787

[51] Int. Cl.³ .................... G01N 31/00; B03C 3/01; B03C 3/14
[52] U.S. Cl. .................................. 73/23; 55/126; 55/135; 55/138; 55/143; 55/270
[58] Field of Search ............... 55/110, 113, 114, 120, 55/124, 126, 135, 137, 138, 141, 143, 145, 146, 270, 481, 117; 73/23

[56] References Cited

U.S. PATENT DOCUMENTS

| 1,573,376 | 2/1926 | Dickerson et al. | 55/145 |
| 2,547,902 | 4/1951 | Burton | 55/110 |
| 2,556,832 | 6/1951 | Vollrath | 55/270 |
| 2,662,608 | 12/1953 | Fields | 55/138 |
| 2,675,090 | 4/1954 | Landgraf | 55/135 |
| 2,789,658 | 4/1957 | Wintermute | 55/145 |
| 3,581,469 | 6/1971 | Davis et al. | 55/270 |
| 3,704,572 | 12/1972 | Gourdine et al. | 55/145 |
| 3,705,478 | 12/1972 | Vaneldik et al. | 55/270 |
| 4,064,548 | 12/1977 | Best et al. | 55/120 |

FOREIGN PATENT DOCUMENTS

931625 7/1963 United Kingdom ............ 55/138

*Primary Examiner*—David L. Lacey
*Attorney, Agent, or Firm*—Silverman, Cass & Singer, Ltd.

[57] ABSTRACT

An exhaust gas analyzer apparatus having a particle filter between its input and the analyzer. The separator includes a heat exchanger coil coupled to a condenser, an electrostatic separator coupled to the condenser, a source of fluid pressure and a filter medium. A valve is provided between the electrostatic separator and the source of fluid pressure so that the electrostatic separator may be scrubbed periodically. The filter medium is interposed between the valve and the analyzer. A source of power is provided. The electrostatic separator includes an ionizing device for charging the gas exhaust particles and two alternating sets of collector electrode plates having differing electric potential collecting the charged particles to enable generally particle free gas to be discharged to the analyzer. One set of electrode plates are connected to the ionizing device and the other set is grounded. The filter medium serves as a secondary filter so as to assure particle free dry gas is delivered to the analyzer.

12 Claims, 3 Drawing Figures

EXHAUST GAS ANALYZER FOR DIESEL ENGINES

BACKGROUND OF THE INVENTION

This invention relates generally to exhaust gas analyzer apparatus preferably for diesel engines, of the type having an inlet connectable to the exhaust of a test engine and including filter means between the exhaust and the gas analyzer device. More particularly, the invention provides improved filter means in the form of an electrostatic separator for assuring delivery of particulate free exhaust gas to said gas analyzer device.

Accurate analysis of exhaust gases from an internal combustion engine, particularly diesel engines, is made difficult due to fine particulate matter such as soot carried by said gases. Such particulate matter quickly fouls the analyzer device. Where the gas analyzer operates on the infra-red absorption principle, the presence of such particulate matter in the gases delivered to the analyzer is of considerable disadvantage.

It is known that to counter such problem, filter means can be placed between the analyzer and the source of the exhaust gases. Since the particulate matter is of fine particle size, the filter medium used must also be fine so as to collect the small soot particles, for example. Accordingly, the filter medium soon becomes clogged, often blocked as to require frequent cleaning and/or replacement.

Thus, a need arises to provide means for removing the fine particulate matter from the exhaust gases prior to delivery to the gas analyzer device, whereby to obviate the disadvantages encountered in use of known devices, and which enables continuous operation of the gas analyzer without requiring change in the filter.

In addition, such filter means must be relatively simple in construction so as to enable inexpensive production and facile and rapid servicing. The particulate removal capacity of such filter device should be substantial so that continuous runs are possible without requiring change of filter or interruption for cleaning, if cleaning is possible.

Another difficulty encountered in the testing of exhaust gases involve the presence of water vapor or particles (droplets) carried by such gases. It would be highly desirable if the filter means employed would include means for separating such water vapor and/or particles from said gases before they reach the gas analyzer device. It would be advantageous also if the filter means could be provided with means for removing the separated particulate matter without dismantling the filter from the test line.

SUMMARY OF THE INVENTION

There is provided for use in exhaust gas analyzer apparatus, particularly for use in analyzing diesel engines, where a filter is interposed between the source of the exhaust gases and a gas analyzing device. The filter comprises an electrostatic separator formed of an ionization electrode and two sets of collector electrodes downstream of said ionization electrode, the sets of collector electrodes being maintained at different electrical potentials, one set relative the other set, said ionization electrode being arranged transverse the direction of flow of the exhaust gases and the collector electrodes arranged parallel the flow of said gases. Means also are provided for cooling the exhaust gases received from the source and for separating water vapor and/or droplets therefrom prior to entry of the gases into the filter.

DESCRIPTION OF PREFERRED EMBODIMENT

Figure 1:
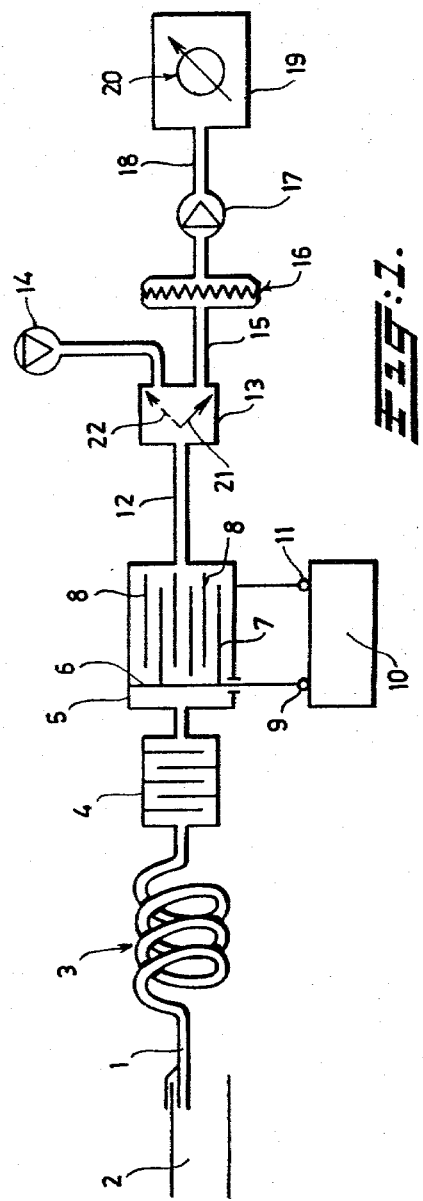
FIG. 1 is a schematic flow diagram of the exhaust gas analyzer apparatus embodying the invention.

The exhaust gas analyzer as defined in the invention consists of a connection pipe 1 which is fastened in the usual manner on the exhaust 2 of the vehicle whose exhaust gases are supposed to be analyzed. The connection pipe 1 is connected to a heat exchanger coil 3, in which the hot exhaust gases are cooled and are directed into a condenser 4 in which the water present in the exhaust gases is removed. The condenser 4 is coupled to an electrostatic separator 5.

Figure 2:
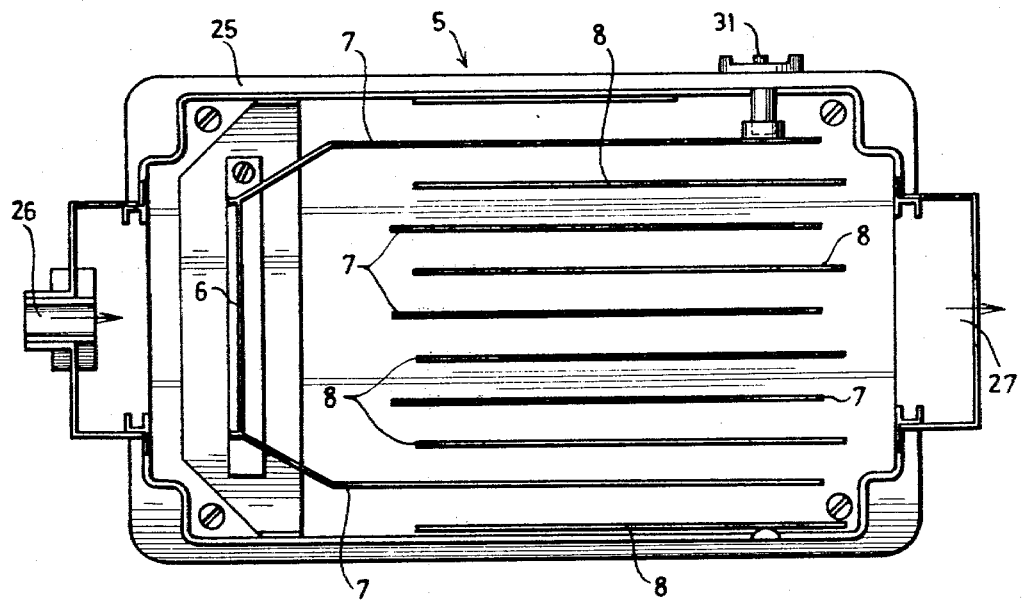
FIG. 2 is a sectional view of the electrostatic filter employed in the apparatus represented in FIG. 1 and viewed looking downward toward the top.
Figure 3:
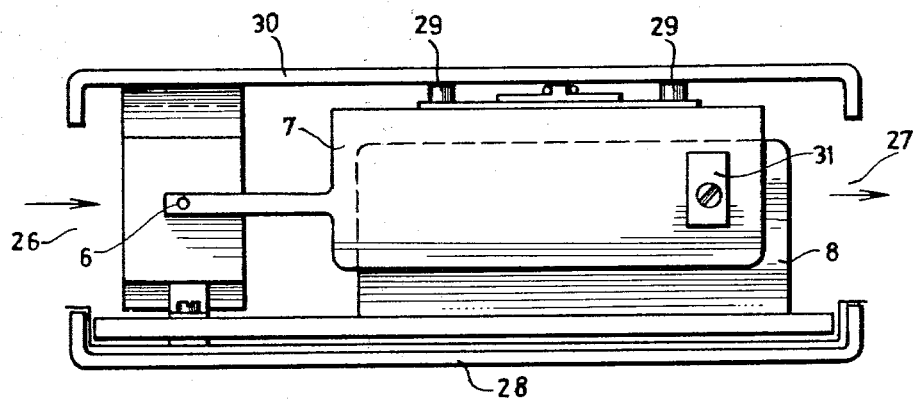
FIG. 3 is a sectional view taken along lines 3—3 of FIG. 2 and viewed in the direction of the arrows, the inlet and outlet portions thereof being deleted.

Referring to FIGS. 2 and 3, it can be seen that electrostatic separator 5 has an ionization electrode 6, a collector electrode 7 connected therewith and grounded collector electrodes 8. The ionization electrode 6 and the collector electrode 7 connected therewith can be connected electrically with the positive pole 9 of a high voltage power source 10 which, for example is capable of supplying a voltage of 10 kV and whose negative connection 11 is grounded. Particulate matter such as soot particles are present in the exhaust gases, particularly gases discharged as exhaust from diesel engines. These soot particles are provided with a positive charge by means of the ionization electrode 6 and, when passing the positive electrode 7, are repulsed by the latter. Grounded electrodes 8 are negative and thus accumulation of the positively charged soot particles takes place on said electrodes 8.

The exhaust gases, which are cleaned in this manner, are connected with a suction pump 17 by way of a two-way valve 13 defining a branch, one leg 14' of which is coupled to a compressed air source 14, the other leg 15 of the branch being coupled to a paper filter 16. Conduit 18 then couples the output of pump 17 to a conventional exhaust gas analyzer 19 having an indicating instrument 20. Preferably the analyzer 19 operates on infra red absorption.

In operation, the suction pump 17 is activated. The exhaust gases are led by means of pump 17 to the analyzer 19 by way of the heat exchanger coil 3, the condenser 4, the electrostatic separator 5 and the two-way valve 13 and the paper filter 16 which functions as a secondary filter. This occurs when the two-way valve 13 is positioned as indicated by a solid line 21. When the two-way valve 13 is operated to the position illustrated by broken line 22, the compressed air source 14, such as a pressure pump, is operated to force surrounding air through the electrostatic filter 5, the condenser 4 and back through heat exchanger coil 3. Not only the electrostatic separator 5 is cleaned but the water which had collected in condenser 4 is led away. Nothing needs to be dismantled.

FIGS. 2 and 3 illustrate the construction of the electrostatic separator 5 in greater detail. Separator 5 includes housing 25 having an inlet 26 and an outlet 27. Housing 25 has a base plate 28 which is grounded, and is connected to negative pole 11 of the voltage source 10. The base plate 28 carries vertically oriented spaced upright parallel electrodes 8 collectively functioning as a grounded collector electrode. Between each electrode 8 is an electrode 7, collectively functioning as a collector electrode. Electrodes 7 are likewise parallel arranged and are connected to the high voltage and also are connected to the ionization electrode wire 6. Electrodes 7 are connected to the upper wall 30 removably coupled to housing 25 by way of insulation elements 29. When the upper wall 30 is removed from housing 25, the collector electrodes 7 are separated from electrodes 8 to facilitate servicing and possibly additional cleaning of the separator 5.

The electrode 6 is disposed transverse the direction of flow of the exhaust gases indicated by arrow 32 while electrodes 7 and 8 are arranged in parallel array and parallel to the direction of flow of said gases. The electrodes 7 are connected with the positive pole of the high voltage source 10 via connector 31. Source 10 provides a voltage of approximately 10 kV referring to the negative pole.

Because electrodes 8 are grounded relative to electrodes 7 which in turn are coupled to electrode wire 6, said electrodes 7 and 8 are maintained at different relative potential. The electrostatic separator 5 not only enables a thorough cleaning of the exhaust gases of particulate matter and moisture but improves the reliability of the analysis.

What we claim is:

1. An exhaust gas analyzer apparatus having a conduit means including an inlet for receiving exhaust gas from an internal combustion engine and an outlet, said apparatus comprising:
   (a) a gas analyzer device connected to the conduit means at the outlet thereof;
   (b) electrostatic filter means interposed in said conduit means between the inlet and the gas analyzer device to receive said gas from said conduit means and to filter said exhaust gas for delivery to said gas analyzer device, said electrostatic filter means comprising ionization electrode means, first and second collector electrode means, an electrical power source and means connecting said electrical power source to said ionization electrode means and to at least one of said first and second collector electrode means;
   (c) a source of pressurized fluid, and
   (d) valve means interposed in said conduit means between said electrostatic filter means and said analyzer device and coupled also to said source of pressurized fluid for selectively controlling flow of said pressurized fluid to said electrostatic filter means and interrupting flow of exhaust gas to said gas analyzing device.

2. The apparatus as claimed in claim 1 further comprising a source of vacuum interposed in said conduit means between said valve means and said gas analyzer device, said valve means having means to selectively control flow of pressurized fluid to said electrostatic filter means or to apply vacuum thereto.

3. The apparatus as claimed in claim 2 further comprising secondary filter means interposed between said source of vacuum and said valve means, said secondary filter means comprising a paper filter.

4. The apparatus as claimed in claim 1 wherein said pressurized fluid is compressed air.

5. The apparatus as claimed in claim 2 wherein the source of vacuum is a suction pump.

6. The apparatus as claimed in claim 1, said valve means having two legs, one leg coupled to said source of pressurized fluid and the other leg interposed in said conduit means and communicating thereby to said gas analyzer device.

7. The apparatus as claimed in claim 6 further including a source of vacuum interposed in said conduit means between said other leg and said gas analyzer device.

8. The apparatus as claimed in claim 7 further comprising secondary filter means interposed in said conduit means between said other leg and said source of vacuum.

9. The apparatus as claimed in claim 1 or 6 wherein said ionization electrode means is an electrode wire disposed transverse the direction of flow of exhaust gas and said first and second collector electrode means are spaced parallel electrodes arranged interleaved alternatively and parallel to said exhaust gas flow.

10. The apparatus as claimed in claim 9 in which one of said first and second electrode means is grounded and the other is connected to said ionizaton electrode means.

11. The apparatus as claimed in claim 1 or 6 wherein condenser means is interposed between the inlet of said conduit means and said electrostatic filter means.

12. The apparatus as claimed in claim 11 wherein a heat exchanger coil is coupled in said conduit means between the inlet and said condenser means.

* * * * *